United States Patent [19]
Watson et al.

[11] Patent Number: 5,994,267
[45] Date of Patent: Nov. 30, 1999

[54] *SCLEROTINIA MINOR* FOR BROAD SPECTRUM BROADLEAF WEED CONTROL

[75] Inventors: Alan K. Watson, Pincourt, Canada; Lee A. Wymore, Oskaloosa, Iowa

[73] Assignee: The Royal Institution for the Advancement of Learning (McGill University), Quebec, Canada

[21] Appl. No.: 08/223,329

[22] Filed: Apr. 5, 1994

Related U.S. Application Data

[63] Continuation of application No. 07/648,179, Feb. 1, 1991, abandoned.

[51] Int. Cl.$^6$ .......................... A01N 63/04; A01N 63/00; A01N 25/26
[52] U.S. Cl. .................... 504/117; 504/100; 71/DIG. 1
[58] Field of Search .................................. 504/100, 117; 71/DIG. 1

[56] References Cited

PUBLICATIONS

Riddle, Gorden E. et al., Virulence of Sclerotinia sclerotiorum and S. minor on Dandelion (Taraxacum officinale), Weed Science, vol. 39, pp. 109–118, 1991.

Riddle, G. E. "Biological Control of Dandelions in Turfgrass Swards by Isolates of *Sclerotinia sclerotiorum* and S. Minor". Masters Thesis, the University of Guelph, Submitted on Jan. 1989, made available to the public on Jun. 13, 1990.

Farr, D.F. et al. "Fungi on Plants and Plant Products in the United States" APS Press, St. Paul (MN), 1989, p. 941.

Hanlin, R.T. "Isolation of Fungi Pathogenic to Weeds" in: Charudattan, R., Biological Control of Weeds with Plant Pathogens (New York, John Wiley & Sons 1982), p. 237.

Hanlin, R.T. "Identification of Plant Pathogenic Fungi" in: Charudattan, R., Biological Control of Weeds with Plant Pathogens (New York, John Wiley & Sons 1982), pp. 237–238.

*Primary Examiner*—John Pak
*Attorney, Agent, or Firm*—Pillsbury Madison & Sutro LLP

[57] ABSTRACT

The present invention is concerned with a novel bioherbicide, and composition thereof for the control of broadleaf weeds in lawns, golf courses, parks, sports fields, other turfed areas, and grass crops such as corn and cereal grains. More specifically, the invention is concerned with a novel isolate *Sclerotinia minor* IMI 344141, agricultural formulations thereof, and its use as a bioherbicide to control troublesome broadleaf weed species.

17 Claims, 2 Drawing Sheets

5,994,267

SCLEROTINIA MINOR FOR BROAD SPECTRUM BROADLEAF WEED CONTROL

This is a continuation of application Ser. No. 07/648,179, filed on Feb. 1, 1991 now abandoned.

FIELD OF THE INVENTION

The present invention is concerned with a novel isolate of *Sclerotinia minor*, namely *Scierotinia minor* IMI 344141 particularly effective as a bioherbicide for the control of a broad spectrum of broadleaf weeds without adversely affecting desirable grass species.

BACKGROUND OF THE INVENTION

Numerous broadleaf weed species, including dandelion (*Taraxacum officinale*), plantain (Plantago species), knotweed (Polygonum species), ground ivy (*Gleocoma hederacea*), ragweed (*Ambrosia artemisiifolia*), white clover (*Trifolium repens*), black medic (*Medicago lupulina*) and henbit (*Lamium amplexicaule*) infest turfgrass areas such as lawns, golf courses, parks and sports fields. Chemical weed control using chemical herbicides is often the easiest, most effective and least expensive way to control broadleaf weeds in turf. Herbicides such as 2,4-D (2,4-dichlorophenoxy acetic acid), mecoprop [2-(4-chloro-2-methylphenoxy) propanoic acid], dichlorprop [2-(2,4-dichlorophenoxy) propanoic acid], dicamba (3,6-dichloro-2-methoxybenzoic acid) and mixtures of these four chemical herbicides are commonly recommended and used to provide broadleaf weed control in turfgrass areas.

There is now significant public concern over the safety and use of chemical herbicides, particularly in the urban environment. These public concerns include toxic chemical residues in soils and water, contamination of foodstuffs, adverse effects on non-target organisms and public health. It would therefore be highly desirable to find a herbicidal composition which has a broad spectrum of activity against troublesome broadleaf weed without damaging desirable grass species, and which has a benign effect on the environment and reduces the input of chemical pesticides.

SUMMARY OF THE INVENTION

In accordance with the present invention, there is now provided a novel isolate of *Sclerotinia minor*, namely *Sclerotinia minor* IMI 344141, which has surprisingly been found to be effective in controlling the growth of undesirable broadleaf weed species without adversely affecting the growth of desirable grass species.

In one aspect of the present invention, there is provided an agricultural composition for controlling the growth of dandelion, plantain, ragweed, velvetleaf, sowthistle, ground ivy, knotweed, chickweed, white clover, and the like, and other undesirable broadleaf weeds in lawns, golf courses, parks, sports fields and in agricultural crops of the Poaceae family, such as corn, wheat, oats and barley and other cereal crops. The novel agricultural composition of the present invention comprises an effective amount of the isolate *Sclerotinia minor* IMI 344141 in association with an agriculturally acceptable carrier.

In another aspect of the present invention, there is provided a method for controlling the growth of undesirable broadleaf weeds in turf and other grass crops by applying an effective amount of a composition containing the isolate *Sclerotinia minor* IMI 344141 preferably in association with an agriculturally acceptable carrier.

DETAILED DESCRIPTION OF THE INVENTION

Figure 1:
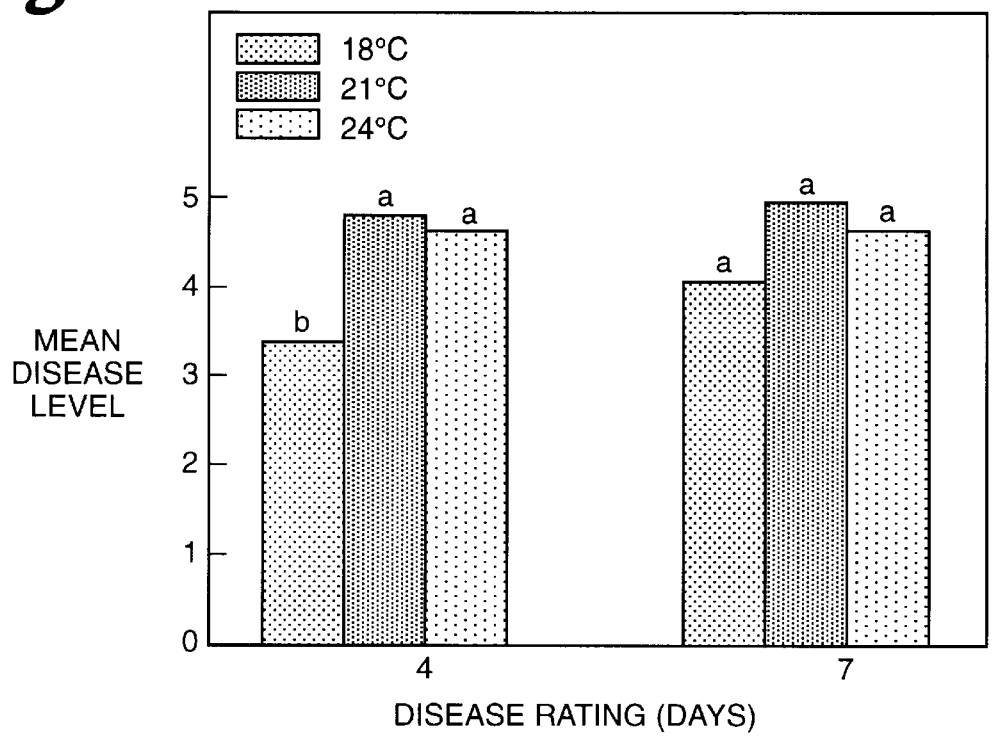
FIG. 1 illustrates the effect of temperature on disease level of dandelion when *Sclerotinia minor* IMI 344141 is applied.
Figure 2:
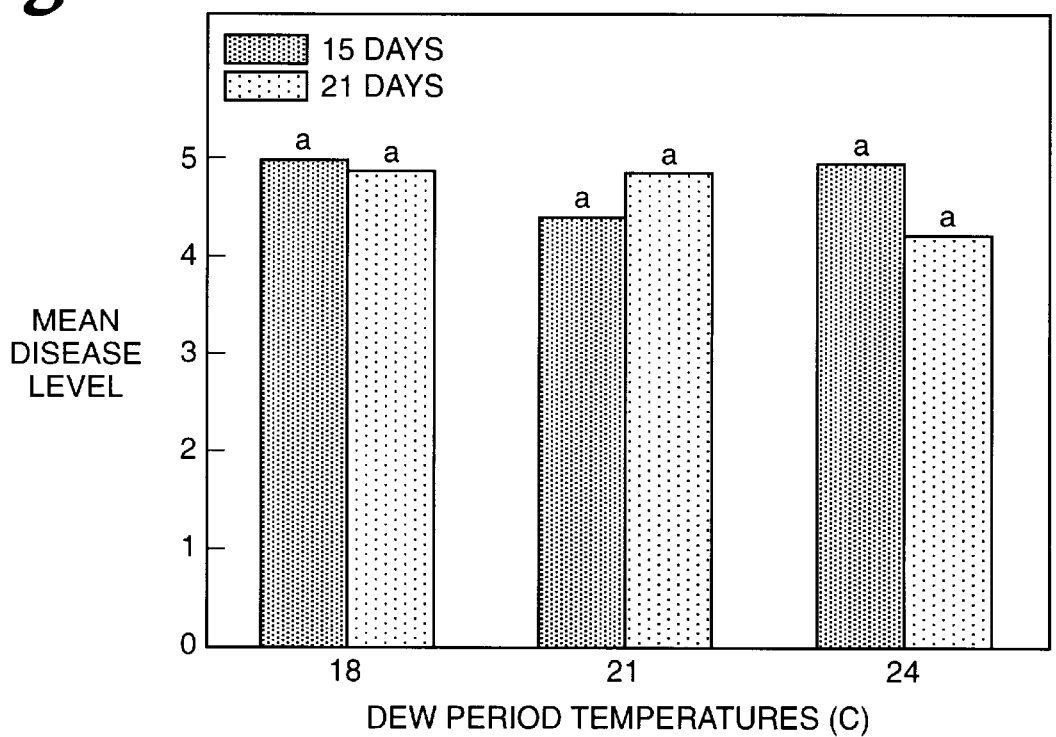
FIG. 2 illustrates the effect of age and temperature on disease level of dandelion when *Sclerotinia minor* IMI 344141 is applied.
Figure 3:
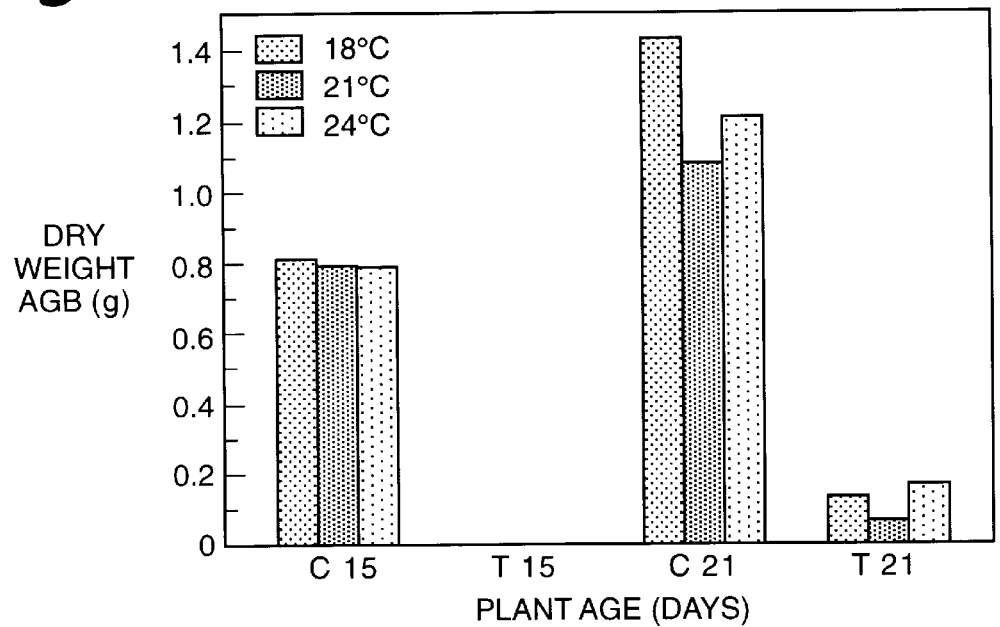
FIG. 3 illustrates the effect of age and temperature on dry weight of above ground biomass of dandelion when *Sclerotinia minor* IMI 344141 is applied.
Figure 4:
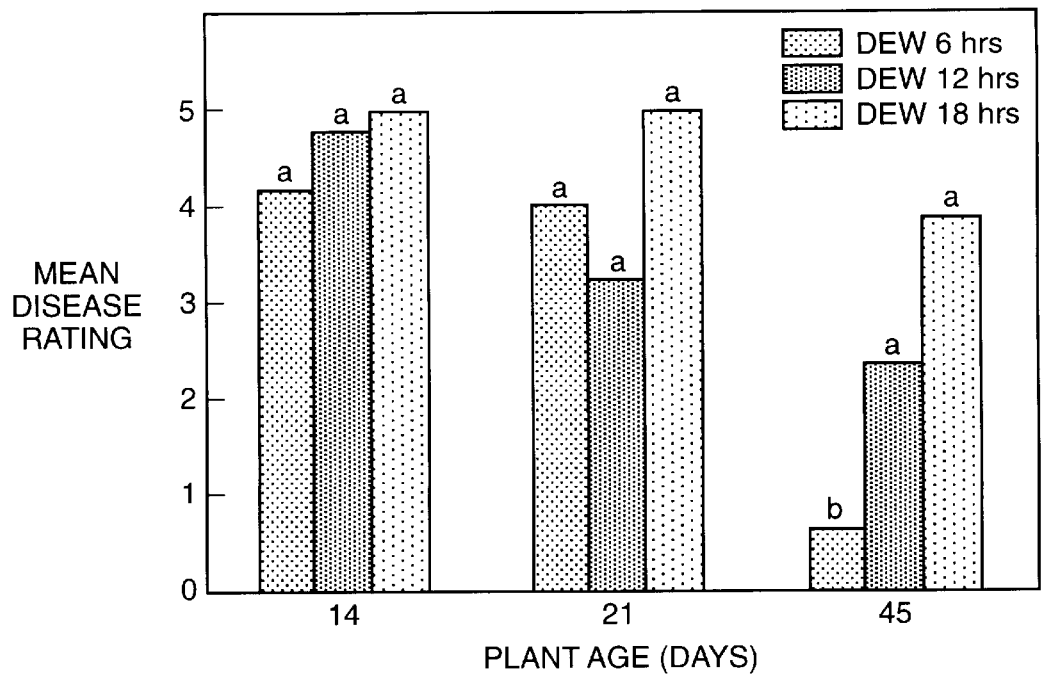
FIG. 4 illustrates the effect of age and dew period on disease level of dandelion when *Sclerotinia minor* IMI 344141 is applied.

Although the merits of using plant pathogens to control weeds in crop production are known for Colletotrichum species (U.S. Pat. No. 3,849,104 and U.S. Pat. No. 3,999,973), Fusarium species (U.S. Pat. No. 4,419,120), Alternaria species (U.S. Pat. No. 4,390,360) and Ascochyta species (U.S. Pat. No. 4,915,724), the use and advantages of using *Sclerotinia minor* and more particularly the isolate *Sclerotinia minor* IMI 344141, has not been demonstrated before. No plant pathogens have been used to date as a bioherbicide to control broadleaf weeds in lawns, golf courses, parks and other turfed areas in the urban environment.

*Sclerotinia minor* Jagger is an inoperculate Discomycetes of the Helotiales order which produces sclerotia, which do not incorporate plant tissues, ascospores in asci in stipitate apothecia, and a superficial Myrioconium microconidial state, but no known disseminative conidia. The small size of the sclerotia and their abundant production scattered over the entire colony on agar media are used as taxonomic characteristics to distinguish *S. minor* from *Sclerotinia sclerotiorum* and *Sclerotinia trifoliorum*. The combination of morphological, microanatomical, and cytological characters clearly demonstrate that these three organisms, *S. minor*, *S. sclerotiorum* and *S. trifoliorum* are distinct.

Although all of these Sclerotinia species have broad host ranges which overlap to some extent, *S. trifoliorum* is generally limited to forage legumes, *S. minor* has been reported as a pathogen of species in Antirrhinum, Apium, Arachis, Brassica, Daucus, Helianthus, Ipomoea, Lactuca, Lycopersicon, Melilotus, Nicotiana, Parthenium, Phaseolus, Solanum, Tragopogon and Tulipa genera, whereas *S. sclerotiorum* has a worldwide distribution and has been reported as pathogenic to species in at least 148 genera (Farr et al. 1989. *Fungi on Plants and Plant Products in the United States*. APS Press, St. Paul).

*S. minor* is an important pathogen of some crops, including lettuce (*Lactuca sativa*), peanut (*Arachis hypogaea*), soybean (*Glycine max*) and sunflower (*Helianthus annus*) and can cause losses of up to 70% of the marketable crop.

*S. minor* has a relatively simple disease cycle. Sclerotia in the soil germinate directly to produce hyphae which infect plants, followed by colonization of the infected plants with the production of more sclerotia on the plant tissues which return to the soil. The sclerotia of *S. minor* can also undergo carpogenic germination to produce apothecia. Apothecia have been reported to occur in nature, but are relatively rare, and therefore are apparently unimportant in the epidemiology of this disease in North America.

A sample of *Sclerotinia minor* Jagger isolate SM-13 has been deposited with the International Mycological Institute in Ferry Lane, Kew, Richmond, Surrey TW9 3AF, United Kingdom, on Jan. 28, 1991, under the Budapest Treaty requirements and has been assigned the accession number IMI 344141.

The deposit is available to the public upon the granting of a patent disclosing it. The deposit is also available as required by foreign patent laws in countries wherein counterparts of the subject application, or its progeny, are filed. However, it should be understood that the availability of a deposit does not constitute a licence to practice the subject invention in derogation of patent rights granted by governmental action.

It is most surprising and unexpected that the isolate of S. minor IMI 344141 of the present invention, which has been obtained from lettuce, has such high bioherbicidal broad spectrum activity on broadleaf weeds, since there is no evidence in the scientific literature that such broadleaf weeds are known to be hosts to S. minor.

It should be noted that S. minor does not normally grow on leaves but rather in soil where eventually it attacks the foliage which touches the soil and thus it would not be expected that if an isolate was applied to broadleaf weeds, they would be attacked to the point of mortality.

It is also surprising that application of the isolate S. minor IMI 344141 of the present invention either alone or in a composition to broadleaf weeds will not damage the surrounding grass species. Accordingly, the isolate S. minor IMI 344141 has the same specificity as known chemical herbicides such as 2,4-D, without the highly undesirable increase in environmental burden.

Application of the Bioherbicide.

The vehicle used to deliver the infection units of S. minor IMI 344141 of the present invention to the targetted weed species was barley or millet grains invaded by fungal mycelium which are essentially various size granules composed of fungal mycelia and autoclaved plant seeds. The application was broadcast as a granule formulation at an equivalent rate of 100 to 300 g/m$^2$.

Any other solid media which would facilitate the growth of mycelia of S. minor would be equally effective. Such media are well known in the art.

Inoculum Production.

Sclerotia of S. minor were dislodged from diseased lettuce tissue and air dried. After surface sterilization, the sclerotia were imbedded in agar (PDA plates) to stimulate germination. The plates were transferred to an incubator set at 21° C. under fluorescent lights. After a four day period the hyphal tips from germinating sclerotia were transferred onto a second set of plates where they grew until the 8.5 cm diameter plate was covered (5 days). Erlenmeyer flasks (250 ml) containing 20 g barley or millet grains and 20 ml water were autoclaved for 20 minutes, cooled, inoculated with mycelium agar plugs (6 mm) from the PDA plates and incubated for 5 days under the same conditions as above. Flasks were shaken everyday to prevent sclerotia formation. Prior to the plant inoculation the inocula was air dried for a period of 2 to 4 hours to obtain individual inoculum units. A constant rate of 2 g/pot of inocula was used throughout the experiments unless otherwise stated. The inoculum was applied in a broadcasting manner over each pot. Pots used for controls received aiutoclaved grains at an equivalent rate of 2 g/pot.

Plant Production.

Seedlings of test plant species were transplanted (one per pot) in a commercialy prepared potting medium such as peat moss in 10-cm plastic pots and grown in controlled environment chambers. The temperature was set at 21° C./18° C. (day/night) and light intensity at 400 $\mu$E m$^{-2}$s$^{-1}$ for 14 hours. Plants were grown for different lengths of time as specified for each experiment. All treatments were replicated from 4 to 16 times in all experiments depending on availability of plant material.

Assessment.

After one, two and three weeks the effect of the pathogen inoculated on plants was visually rated on a scale of 0 to 5. The proportion of healthy vs diseased tissue served as a means to determine the efficacy of the fungus under set conditions. The statistical analysis performed on the data was a Kruskal-Wallis analysis followed by a multiple comparison test to locate differences among treatments. Plants were kept for further evaluations and in some cases assessment of dry weight of above ground biomass was taken after the third disease rating.

The present invention will be further illustrated by the following examples, which are representative, and do not restrict the scope of the invention in any way.

EXAMPLE 1

Preliminary Experiment.

A greenhouse experiment was set up to evaluate the ability of various Sclerotinia species to suppress the growth of broadleaf weeds. Isolates of the genus S. minor, S. sclerotiorum and S. trifoliorum were tested on different weeds including dandelion (*Taraxacum officinale*), plantain (*Plantago major*), ground ivy (*Glecoma hederacea*), and on bluegrass (*Poa pratensis*) a common desirable grass species in turf. Soil plugs from the campus lawn were removed and transferred into 12,5-cm plastic pots. Each pot contained blue grass and a number of weed species with one being predominant. All pots were placed in a mist frame after receiving 3,5 g/pot of inoculated barley grains. A continuous mist was applied for a 6 hour period during the night. The greenhouse temperature was approximately 23±5° C. The results are summarized in Table 1.

TABLE 1

Effect of different isolates of Sclerotinia on various weeds and on blue grass.

| | Mean disease level[a] | | | | | |
|---|---|---|---|---|---|---|
| | Trial # 1 Isolates[b] | | | Trial # 2 Isolates[b] | | |
| Host Name | 1 | 11 | 13 | 1 | 11 | 13 |
| *Taraxacum officinale* | 2 | 3 | 4 | 3 | 4 | 5 |
| *Plantago major* | 4 | 2 | 5 | 2 | 2 | 5 |
| *Glecoma hederacea* | 0 | 0 | 2 | 1 | 1 | 3 |
| *Poa pratensis* | 0 | 0 | 0 | 0 | 0 | 0 |

[a]Disease rating scale: 0: no disease, 1: 1-25% of necrotic tissue, 2: 26-50%, 3: 51-75%, 4: 76-99%, 5: dead plants.
[b]Isolate #1: S. trifoliorum
Isolate #11: S. sclerotiorum
Isolate #13: S. minor IMI 344141 of the present invention In this experiment, isolate of S. minor IMI 344141 consistently caused the greatest amount of disease on the three weed species tested as illustrated in Table 1. The desirable grass species Poa pratensis was not affected by S. minor.

Therefore, S. minor IMI 344141, was the isolate selected for further evaluation. It severely damaged or killed the broadleaf weed species without any harm to the grass crops.

EXAMPLE 2

Experiments were conducted to evaluate the effect of the age of the host plant and environmental parameters of dew period duration and dew period temperatures on disease development caused by *S. minor* IMI 344141 when inoculated onto dandelion. The experimental variables are given in Table 2.

TABLE 2

Post Inoculation Variables For Dandelion Experiments.

| Experiment # | Inoculum carrier | Host age (days) | Dew period duration (hrs) | Dew period temperature (° C.) |
|---|---|---|---|---|
| 1 | Barley | 17 | 18 | 18, 21, 24 |
| 2 | Barley | 15, 21 | 18 | 18, 21, 24 |
| 3 | Barley | 14, 21, 45 | 6, 12, 18 | 21 |

In experiment #1, the dandelion plants were rapidly and severely affected by *S. minor* IMI 344141 (FIG. 1) with most plants killed or severely damaged after 4 days. The level of disease was greater when the dew period temperature was 21° C., but high levels of disease occurred at cooler (18° C.) and warmer (24° C.) temperatures.

In a similar experiment #2, disease level was very high over all dew period temperatures tested and there was no significant differences between two-week-old and three-week-old dandelion plants, both ages were equally susceptible to *S. minor* IMI 344141 (FIG. 2). The effect of the bioherbicide on dandelion control is clearly illustrated in FIG. 3 where the biomass of control (C) and treated (T) are compared. Two-week-old dandelion plants are killed by the treatment under all three dew-period temperatures tested and essentially all of the above-ground biomass is also destroyed when treated at the three-week-old stage.

In experiment #3, even when the dew period is relatively short (6 hr), extensive disease develops on two-week-old seedlings (FIG. 4). Dew-period duration appears to have a greater effect when the plant is three weeks old, although the results are not statistically different according to the analysis used. However, as the dandelion plants mature (45 days old), the longer dew periods provide higher disease levels.

EXAMPLE 3

Similar experiments as to those described in Example 1 and 2 on dandelion plants were conducted on the following additional broadleaf species: *Plantago major, Ambrosia artemisiifolia, Plantago lanceolata, Sonchus arvensis, Polygonum aviculare, Trifolium repens, Glecoma hederacea*, Oxalis sp *and Cerastium vulgatum*. The plants tested, their age, the inoculum type, the dew-period duration and dew-period temperature, and the results are summarized in Table 3.

TABLE 3

Experiments using *Sclerotinia minor* IMI 344141 (isolate #13) on weed species other than dandelion.

| Host | Age (host) (days) | Inoculum | Dew period (Time) | Dew period (° C.) | Mortality (%) | Mean Disease Rating (0–5)[a] |
|---|---|---|---|---|---|---|
| *Plantago major* | 27 | whole barley | 12 hrs | 21 | 100 | 5 |
| | | cracked barley | 12 hrs | 21 | 100 | 5 |
| | 32 | whole barley | 6 hrs | 21 | 33 | 3.0 |
| | | | 12 hrs | 21 | 33 | 2.7 |
| | | | 18 hrs | 21 | 100 | 5 |
| | 34 | whole barley | 12 hrs | 18 | 40 | 3.5 |
| | | | | 21 | 25 | 3.7 |
| | | | | 24 | 30 | 3.6 |
| | 34 | whole barley | 18 hrs | 18 | 70 | 4.4 |
| | | | | 21 | 90 | 4.8 |
| | | | | 24 | 50 | 4.2 |
| | 38 | whole barley | —[b] | — | 17 | 3.2 |
| | | | 6 hrs | 21 | 20 | 3.5 |
| | | cracked barley | — | — | 17 | 2.8 |
| | | | 6 hrs | 21 | 80 | 4.3 |
| | 45 | whole barley | 24 hrs | 21 | 100 | 5 |
| *Ambrosla artemisiifolia* | 23 | whole barley | 12 hrs | 21 | 100 | 5 |
| | | cracked barley | 12 hrs | 21 | 89 | 4.9 |
| | 37 | whole barley | 18 hrs | 21 | 46 | 3.1 |
| | 40 | whole barley | 6 hrs | 21 | 0 | 2.0 |
| | | | 12 hrs | 21 | 0 | 1.5 |
| *Plantago lanceolata* | 30 | cracked barley | — | — | 50 | 3.5 |
| | | | 6 hrs | 21 | 25 | 2.0 |
| | | | 12 hrs | 21 | 20 | 2.2 |
| | | | 18 hrs | 21 | 40 | 2.8 |
| *Sonchus arvensis* | 22 | cracked barley | 12 hrs | 21 | 100 | 5 |
| | | | 18 hrs | 21 | 100 | 5 |
| *Polygonum aviculare* | 13 | cracked barley | — | — | 0 | 0 |
| | | | 6 hrs | 21 | 0 | 0 |
| | | | 12 hrs | 21 | 33 | 1.7 |
| | | | 18 hrs | 21 | 0 | 0 |
| | 28 | cracked barley | — | — | 0 | 0 |
| | | | 18 hrs | 21 | 25 | 1.3 |
| | | whole barley | — | — | 0 | 0 |
| | | | 18 hrs | 21 | 75 | 4.0 |
| | 43 | whole barley | 18 hrs | 21 | 50 | 3.3 |
| *Trifolium repens* | 27 | cracked barley | — | — | 0 | 3.0 |
| | | | 6 hrs | 21 | 33 | 4.0 |
| | | | 12 hrs | 21 | 0 | 2.0 |
| | | | 18 hrs | 21 | 33 | 3.0 |
| *Glecoma hederacea* | 10 | cracked barley | 6 hrs | 21 | 0 | 0 |
| | | | 12 hrs | 21 | 0 | 0.8 |
| | | | 18 hrs | 21 | 0 | 0.5 |
| | 23 | cracked barley | — | — | 0 | 0.3 |
| | | | 18 hrs | 21 | 0 | 0.3 |
| | | whole barley | — | — | 0 | 0 |
| | | | 18 hrs | 21 | 0 | 0 |
| | 45 | whole barley | 24 hrs | 21 | 50 | 4.0 |
| *Oxalis sp* | 28 | cracked barley | — | — | 0 | 0.3 |
| | | | 18 hrs | 24 | 0 | 0.3 |

TABLE 3-continued

Experiments using *Sclerotinia minor* IMI 344141 (isolate #13) on weed species other than dandelion.

| Host | Age (host) (days) | Inoculum | Dew period (Time) | (° C.) | Mortality (%) | Mean Disease Rating (0–5)[a] |
|---|---|---|---|---|---|---|
| Cerastium vulgatum | 45 | whole barley | 24 hrs | 21 | 0 | 3.0 |

[a]Disease rating scale: 0 - no disease, 1 - 1 to 25% necrotic tissue 1 2 - 26 to 50% necrotic tissue, 3 - 51 to 75% necrotic tissue, 4 - 76 to 99% necrotic tissue, and 5 - dead plants.
[b]—did not receive a dew period.

All weed species tested, with the exception of the Oxalis sp. were susceptible to *S. minor* IMI 344141 and were severely damaged or destroyed. Mortality and disease rating were higher when plants received a relatively long dew period ($\geq 18$ hr) at a relatively warm temperature ($\geq 21°$ C.). Older plants tended to be more tolerant to the disease.

The embodiments ofd the invention ion which exclusive property or privilege is claimed are defined as follows:

1. A method for controlling the growth of broadleaf weed species in turfgrass and in agricultural grass crops, comprising applying to said broadleaf weed species an effective amount of the isolate *Sclerotinia minor* IMI 344141 to effect and produce typical foliar wilt and rot in said broadleaf weed species so as to inhibit their growth.

2. The method as claimed in claim 1, wherein said broadleaf weed species is dandelion.

3. The method as claimed in claim 1, wherein said broadleaf weed species is broadleaf plantain.

4. The method as claimed in claim 1, wherein said broadleaf weed species is ragweed.

5. The method as claimed in claim 1, wherein said broadleaf weed species is ground ivy.

6. The method as claimed in claim 1, wherein said broadleaf weed species is knotweed.

7. The method as claimed in claim 1, wherein said broadleaf weed species is sow thistle.

8. The method as claimed in claim 1, wherein said broadleaf weed species is white clover.

9. The method as claimed in claim 1 wherein *Scierotinia minor* IMI 344141 is applied in the form of a pellet comprised of barley grains or millet grains impregnated with fungal mycelium.

10. The method according to claim 1, wherein the isolate *Sclerotinia minor* IMI 344141 is applied as granules comprising autoclaved plant seeds invaded by the isolate mycelium.

11. The method according to claim 10, wherein said granules are applied at a rate of 100 to 300 g/m$^2$.

12. The method according to claim 11, wherein said broadleaf weed species is dandelion.

13. The method according to claim 12, wherein the time necessary to control said dandelion is between 4 days and 21 days.

14. The method according to claim 10, wherein said plant seeds are barley seeds.

15. A composition for controlling the growth of broadleaf weed species in turf grass and in agricultural grass crops comprising an effective amount of the isolate *Sclerotinia minor* IMI 344141 in association with an agricultural acceptable carrier.

16. The composition according to claim 15, which consists essentially of granules comprising autoclaved plant seeds invaded by the isolate mycelium.

17. The composition according to claim 16, wherein said plant seeds are barley seeds.

* * * * *